United States Patent
Bredno et al.

(10) Patent No.: US 9,153,012 B2
(45) Date of Patent: Oct. 6, 2015

(54) DIAGNOSTIC IMAGE FEATURES CLOSE TO ARTIFACT SOURCES

(75) Inventors: Joerg Bredno, San Francisco, CA (US); Sven Prevrhal, San Francisco, CA (US); Eberhard Sevastian Hansis, Menlo Park, CA (US); David Sowards-Emmerd, San Jose, CA (US)

(73) Assignee: Koninklijke Philips N.V., Eindhoven (NL)

( * ) Notice: Subject to any disclaimer, the term of this patent is extended or adjusted under 35 U.S.C. 154(b) by 208 days.

(21) Appl. No.: 13/989,152

(22) PCT Filed: Nov. 22, 2011

(86) PCT No.: PCT/IB2011/055233
§ 371 (c)(1),
(2), (4) Date: May 23, 2013

(87) PCT Pub. No.: WO2012/073151
PCT Pub. Date: Jun. 7, 2012

(65) Prior Publication Data
US 2013/0243298 A1    Sep. 19, 2013

Related U.S. Application Data

(60) Provisional application No. 61/418,420, filed on Dec. 1, 2010.

(51) Int. Cl.
*G06K 9/00* (2006.01)
*G06T 5/00* (2006.01)
*G06T 5/50* (2006.01)
*G06T 11/00* (2006.01)
*A61B 6/00* (2006.01)

(52) U.S. Cl.
CPC ............ *G06T 5/00* (2013.01); *A61B 6/5258* (2013.01); *G06T 5/50* (2013.01); *G06T 11/008* (2013.01); *G06T 2207/10072* (2013.01)

(58) Field of Classification Search
None
See application file for complete search history.

(56) References Cited

U.S. PATENT DOCUMENTS

| | | |
|---|---|---|
| 6,691,134 B1 | 2/2004 | Babula et al. |
| 7,374,077 B2 | 5/2008 | Shimura |
| 7,720,931 B2 | 5/2010 | Mei et al. |
| 2003/0112921 A1* | 6/2003 | Lang et al. ............... 378/54 |
| 2003/0156684 A1 | 8/2003 | Fessler |
| 2004/0013294 A1* | 1/2004 | Bernard De Man et al. . 382/132 |
| 2005/0143654 A1* | 6/2005 | Zuiderveld et al. .......... 600/443 |
| 2006/0210131 A1* | 9/2006 | Wheeler et al. .............. 382/128 |
| 2007/0003118 A1* | 1/2007 | Wheeler et al. .............. 382/128 |
| 2007/0081712 A1* | 4/2007 | Huang et al. ................. 382/128 |
| 2007/0133736 A1 | 6/2007 | Chen et al. |
| 2008/0100612 A1* | 5/2008 | Dastmalchi et al. ......... 345/418 |
| 2008/0267474 A1 | 10/2008 | Chen et al. |
| 2009/0003514 A1* | 1/2009 | Edic et al. ..................... 378/10 |

(Continued)

*Primary Examiner* — Shervin Nakhjavan

(57) ABSTRACT

When correcting for artifacts on an attenuation map caused by an artifact source in a computed tomography image, nuclear images are reconstructed two or more times, each time using a different correction technique or uncorrected attenuation data. Corresponding voxels in the reconstructed images are compared to identify local areas that change, i.e., are fragile and therefore low-confidence, and areas that do not vary or exhibit little variance among the plurality of reconstructed images and are thus accorded a higher confidence. The reconstructed nuclear image is overlaid with color encoding indicative of the amount of confidence accorded to each voxel value obtained by attenuation-corrected tomographic reconstruction.

31 Claims, 8 Drawing Sheets

(56) References Cited

U.S. PATENT DOCUMENTS

| | | | |
|---|---|---|---|
| 2009/0136112 A1* | 5/2009 | Bismuth et al. | 382/132 |
| 2009/0201291 A1* | 8/2009 | Ziv et al. | 345/424 |
| 2009/0234626 A1* | 9/2009 | Yu et al. | 703/11 |
| 2009/0253980 A1* | 10/2009 | Wollenweber et al. | 600/411 |
| 2009/0257621 A1* | 10/2009 | Silver | 382/103 |
| 2012/0027297 A1* | 2/2012 | Feris et al. | 382/173 |
| 2012/0051664 A1* | 3/2012 | Gopalakrishnan et al. | 382/294 |
| 2013/0004050 A1* | 1/2013 | Wu et al. | 382/132 |

* cited by examiner

DIAGNOSTIC IMAGE FEATURES CLOSE TO ARTIFACT SOURCES

CROSS REFERENCE TO RELATED APPLICATIONS

This application is a national filing of PCT application Serial No. PCT/IB2011/055233, filed Nov. 22, 2011, published as WO 2012/073151 A2 on Jun. 7, 2012, which claims the benefit of U.S. provisional application Ser. No. 61/418,420 filed Dec. 1, 2010, which is incorporated herein by reference.

DESCRIPTION

The present innovation finds application in tomographic imaging systems, particularly with regard to artifact reduction therein. However, it will be appreciated that the described techniques may also find application in other imaging systems, other artifact reduction scenarios, other image quality improvement techniques, and the like.

For tomographic modalities, e.g., Computed Tomography (CT), Positron-Emission Tomography (PET) or Single-Photon Emission Computed Tomography (SPECT), tomographic reconstruction provides local measurements from within the body of a patient. Diagnostic information is obtained from quantitative and qualitative information such as uptake of a radioactive tracer or x-ray attenuation and the spatial distribution of these values, which is the reconstructed image data. For all tomographic modalities, artifact sources are known and can lead to a degradation of image quality or total loss of reliable quantitative information. Prominent artifact sources such as metal implants and other highly opaque structures lead to reduced image quality for all above modalities, and the resulting image artifacts have impact both locally around the implant (e.g., blooming) and in other image regions (e.g., streaks).

For some clinical applications, the image data close to an artifact source is of major interest. One example is the assessment of the long-term stability of an orthopedic implant and its host bone environment. A combined PET-CT scan can reveal degradation of the implant's fixation to bone in a twofold manner: An increase in the local PET tracer concentration around the implant is indicative of metabolic processes that include degrading bone restructuring; a decrease in the CT signal close to the implant is indicative of a loss of bone density. Together, this information allows the assessment of the risk of implant failure. For such an application, image information close to the implant is of major interest, but with the implant being an artifact source, this image information is also least reliable.

The present application provides new and improved systems and methods for assessing and reducing uncertainty in structural and functional image data after tomographic reconstruction with or without attenuation correction in the presence of image artifacts, which overcome the above-referenced problems and others.

In accordance with one aspect, a method of improving tomographic image quality comprises automatically binning tomographic values based on application specific bins defined as a function of an artifact source, correcting artifacts in the reconstructed image by adjusting voxel values affected by the artifacts in the reconstructed image, and generating a confidence map comprising a confidence value for adjusted voxels in each of the bins.

In accordance with another aspect, a method of generating a confidence map for a nuclear emission image that is attenuation-corrected using structural image data comprises generating a first attenuation map from the originally acquired structural image data, executing an artifact reduction method on the structural image data to generate artifact-reduced structural image data, and generating a second attenuation map from the artifact-reduced structural image data. The method further comprises executing a first attenuation-corrected reconstruction protocol that reconstructs a set of nuclear emission scan data using the first attenuation map to generate a first attenuation-corrected reconstructed nuclear image, executing a second attenuation-corrected reconstruction protocol that reconstructs the set of nuclear scan data using the second attenuation map to generate a second attenuation-corrected reconstructed nuclear image, and comparing the first and second attenuation-corrected reconstructed nuclear images to identify local differences therein that are introduced by artifacts in the structural image data. Additionally, the method comprises generating a confidence map for the attenuation-corrected nuclear images, the confidence map comprising the local confidence value for each corrected image element in the second attenuation-corrected nuclear image, the local confidence value being identified as a function of the difference in the first and second reconstructed nuclear emission data and one or more user-selected parameters, and displaying the confidence map overlaid on the first or the second attenuation-corrected nuclear image to a user.

According to another aspect, a system that facilitates generating a confidence map for a nuclear image that is attenuation-corrected using structural scan data comprises a processor programmed to execute a nuclear confidence map generation module stored in a computer-readable medium and comprising instructions for generating a first attenuation map from acquired structural image data, and executing an artifact reduction protocol on the structural image data to generate artifact-reduced structural image data. The instructions further comprise generating a second attenuation map from the artifact-corrected structural image data, executing a first attenuation-corrected reconstruction protocol that reconstructs a set of nuclear emission scan data using the first attenuation map to generate a first attenuation-corrected reconstructed nuclear image, and executing a second attenuation-corrected reconstruction protocol that reconstructs the set of nuclear emission scan data using the second attenuation map to generate a second attenuation-corrected reconstructed nuclear image. Additionally, the instructions comprise comparing the first and second attenuation-corrected reconstructed nuclear images to identify local differences therein that are introduced by artifacts in the structural image data, and generating a confidence map for the first or second attenuation-corrected nuclear image, the confidence map comprising the local confidence value for each voxel in the second attenuation-corrected nuclear image, the local confidence value being identified as a function of the local differences in the two reconstructed nuclear emission images and one or more user-selected parameters. Moreover, the instructions comprise displaying the confidence map overlaid on the first or the second attenuation-corrected nuclear image on a display to a user.

According to another aspect, a method for improving data reliability for tomographic image data near an artifact source comprises segmenting an anatomical image comprising an artifact source, estimating an impact of the artifact source as a local loss of confidence in image voxel values, identifying trusted regions of the image that are not affected by the artifact source, and selecting a binning strategy for binning similar regions in a reconstructed image together as a function of a clinical application and one or more user-selected parameters. The method further comprises identifying all voxels in each of a plurality of bins generated by the binning strategy, averaging the contribution estimates for all voxels in each bin using local confidence values as weighting during averaging, and presenting binned image data to a user on a display.

In accordance with another aspect, a method for providing an improved measurement for a region comprising voxels with low confidence values comprises segmenting an anatomical image comprising an artifact source, estimating an impact of the artifact source as a local loss of confidence in image voxel values, and selecting a binning strategy for binning similar regions in a reconstructed image together as a function of a clinical application and one or more user-selected parameters. The method further comprises collecting, from input projection data, projection rays that pass through a low confidence region, assigning a confidence value to each projection ray, and computing a set of new measurements for the low confidence region by removing all contributions to the projection rays from reconstructed image data outside of the low confidence region and assigning the remaining contributions to the low confidence region and computing a final measurement for the low confidence region as weighted average of the set of new measurements and the image region value. The weighting function used in the weighted average can be determined from the confidence value assigned to the image region, e.g., assigning a lower weight to the image region and a higher weight to the ray contributions if the image region's confidence is low, and and/or from a confidence value assigned to each projection ray, e.g., assigning a lower confidence to rays that passed through substantial amounts of metal.

One advantage is that the confidence in the quantitative accuracy of a certain reconstructed image region can be displayed to the user.

Another advantage is that image quality and quantitative image accuracy is improved.

Another advantage is that improved quantization can be performed for artifact-affected image region.

Still further advantages of the subject innovation will be appreciated by those of ordinary skill in the art upon reading and understand the following detailed description.

The drawings are only for purposes of illustrating various aspects and are not to be construed as limiting.

The described systems and methods compensate the reduced reliability of image information close to diagnostically relevant artifact sources by automatically binning tomographic values based on application-specific bins that are defined by the object of interest, which is also an artifact source, and the application at hand. In one example, a processing application can additionally present bone density as a function of distance to the implant, and metabolic activity as a function of distance to the implant. Using methods described herein, this binning can re-introduce reliability in the measurements affected by image artifacts.

More generally, the innovation relates to imaging modalities that create tomographic structural or anatomical information (X-Ray computed tomography CT, Cone-beam or flat-panel X-Ray computed tomography CBCT, magnetic resonance imaging MRI and others), often from a set of projection input data. Additionally, nuclear emission imaging modalities are provided that create tomographic functional or emission information (SPECT or PET) from a set of emission input data. For the reconstruction of tomographic emission images, information on the local attenuation of radiation in an imaged object or patient is desired. This information is provided by a structural or anatomical tomographic image that is input to the creation of an attenuation map. Such an attenuation map is then input to the attenuation-corrected tomographic reconstruction of emission data. Tomographic image data is also referred to herein as reconstructed image data.

For all tomographic modalities, metal implants and other highly opaque objects lead to artifacts and degraded image quality, particularly in the immediate vicinity of the opaque object. This is a problem in many clinical applications, for instance in assessment of bone quality around orthopedic implants. To overcome this problem, the described systems and methods provide information about the reliability of image data to the user as an additional diagnostic aid. Such confidence or reliability measures are computed by different methods described below. The reliability or confidence is increased in the presence of a clinical application by statistical binning of the image data over larger regions that contain affected and non-affected regions. For example, plots for "average bone density depending on distance to the implant" and for "average metabolic activity depending on distance to the implant" can re-introduce reliability in the measurements affected by image artifacts. The described systems and methods can be implemented using a number of clinical workstation applications and is beneficial for combination modalities such as, SPECT-CT, PET-CT, etc.

Figure 1:
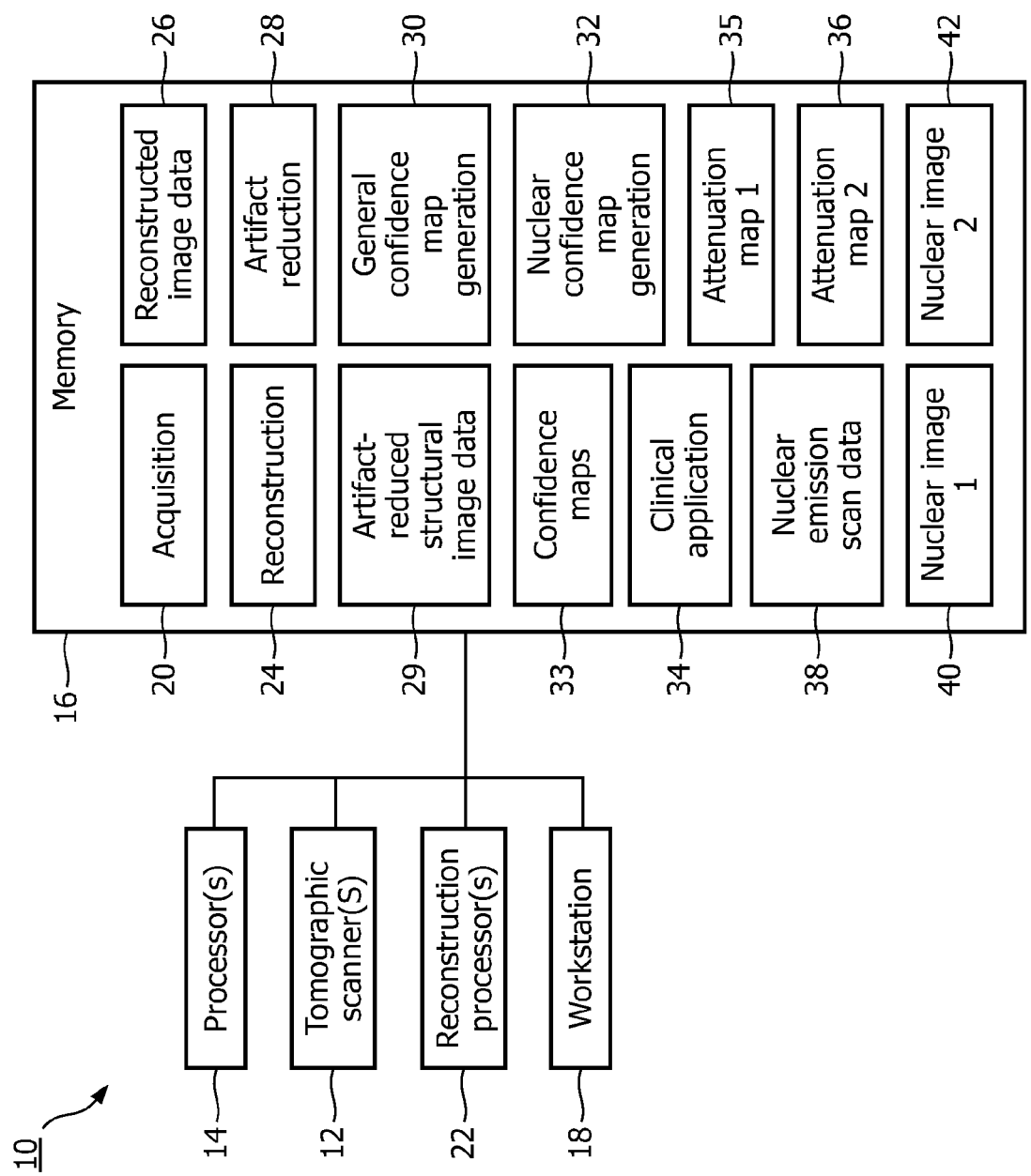
FIG. 1 illustrates a system that facilitates improving data reliability or confidence for tomographic image data near an artifact source (e.g., a metal implant or the like).

FIG. 1 illustrates a system 10 that facilitates improving data reliability or confidence for tomographic image data near an artifact source (e.g., a metal implant or the like). The system 10 comprises one or more tomographic scanners (e.g., CT, CBCT, MRI, PET, SPECT, etc.) that scan a subject or patient to acquire scan data. A processor 14 executes, and a memory 16 stores, computer-executable instructions for performing the various functions, methods, techniques, etc., described herein. The system also comprises a workstation 18 via which a user enters and/or manipulates data in the system, and via which information is displayed to the user.

The processor 14 executes an acquisition module 20 (e.g., a set of computer-executable instructions, a routine, program, or the like) stored in the memory 16 to acquire tomographic scan data of the subject. A reconstruction processor 22 executes a reconstruction module or algorithm 24 stored in the memory 16 to reconstruct the acquired image data into a reconstructed image 26. The processor executes one or more artifact reduction modules 28 to reduce artifacts in the reconstructed image, thereby generating artifact-reduced structural image data 29. The processor additionally executes one or more of a general confidence map generation module 30 and a nuclear confidence map generation module 32 to generate confidence maps 33 that show a level of confidence in the image values of reconstructed image data. The confidence maps are color coded and overlaid on the reconstructed image when displayed to a user on a display (not shown) of the workstation 18. The confidence maps are also employed when the processor executes a clinical application module 34 that applies the confidence maps to increase reliability for a clinical application using confidence maps and one or more user-selected criteria. The confidence map generation modules 30, 32, and the clinical application module 34 are described in greater detail with regard to FIGS. 2-4.

According to an example, structural image data, here preferably CT scan data of a volume of interest is acquired, and a first attenuation map 35 is generated from the reconstructed the structural image data. Image artifacts in the acquired structural data are reduced, e.g., by the artifact reduction module 28, and a second attenuation map 36 is generated from this data. Acquired nuclear emission scan data 38 (e.g., PET, SPECT, etc.) of the volume of interest is then reconstructed twice using the attenuation maps 35, 36: once using the first attenuation map, and again using the second attenuation map, to generate first and second reconstructed nuclear emission images 40, 42, respectively. The nuclear images are compared to detect local differences there between, which may be caused by artifacts in the original acquired structural image data. The nuclear confidence map generation module 32 generates a confidence map 33, which includes information related to the likelihood that the corrected voxels in the second nuclear image are reliable, as a function of the detected local differences. In another embodiment, the first and second attenuation maps are generated using two different reconstruction methods or artifact reduction techniques.

It will be understood that the processor 14 executes, and the memory 16 stores, computer executable instructions for carrying out the various functions and/or methods described herein. The memory 16 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 14 can read and execute. In this context, the system 10 may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphics processing unit (GPU), or PAL, or the like.

Figure 2:
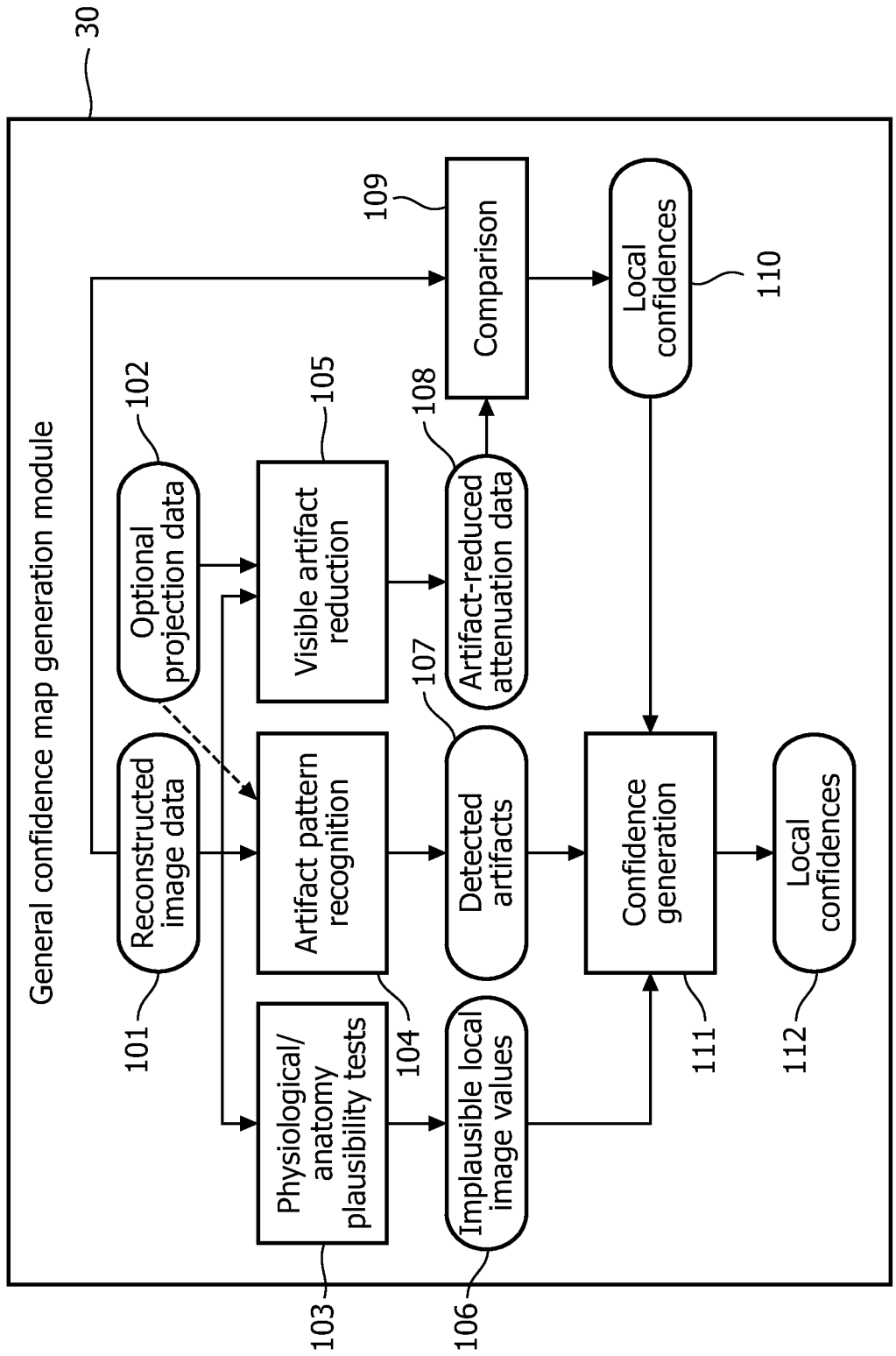
FIG. 2 illustrates the general confidence maps module, which generates confidence maps that indicate the local reliability of image data that is in close proximity and in distance to an artifact source.

FIG. 2 illustrates the general confidence map generation module 30, which generates confidence maps that indicate the local reliability of image data that is in close proximity or distance to an artifact source. Reconstructed image data 101 and optional projection data 102 is input to different processing modules or algorithms that extract different aspects of reduced confidence in image data. As used herein, "module" refers to a set of computer-executable instructions that are executed by a processor, a computer routine or subroutine, a computer program, or the like, for performing the various functions, techniques, methods, etc., described herein. A physiological and anatomy plausibility test module 103 compares reconstructed image voxel data (e.g., Hounsfield values for a CT acquisition) to expected values for the image voxel data and patient anatomy at hand. Comparison to atlas data and expected image values by the test module identifies implausible local image values 106. A dedicated artifact pattern recognition module 104 searches for streaks and/or blooming artifacts 107 or other structures in the image 101 that are indicative of or similar to those created by a known or assumed artifact source in the image at hand. Additionally, any known state of the art method can be applied to the image by a visible artifact reduction module 105, which reduces visible artifacts in the image. The resulting artifact-reduced attenuation data 108 is compared to the original input data 101 to determine local differences or corrections 110 in image values. The detected implausible image values, artifact patterns, and the changes introduced by the visible artifact reduction are input to the confidence generation module 111, which fuses these individual contributions into a local measure of confidence 112 and generates a confidence map comprising a confidence value for each voxel that is determined as a function of the individual contributions and one or more user-selected parameters that control how the contributions from each of the implausible local values 106, the detected artifacts 107, and the applied local corrections 110 are weighted or combined to generate a final confidence measure. The confidence map is then overlaid on one or more of the reconstructed images and presented to the user.

Figure 3:
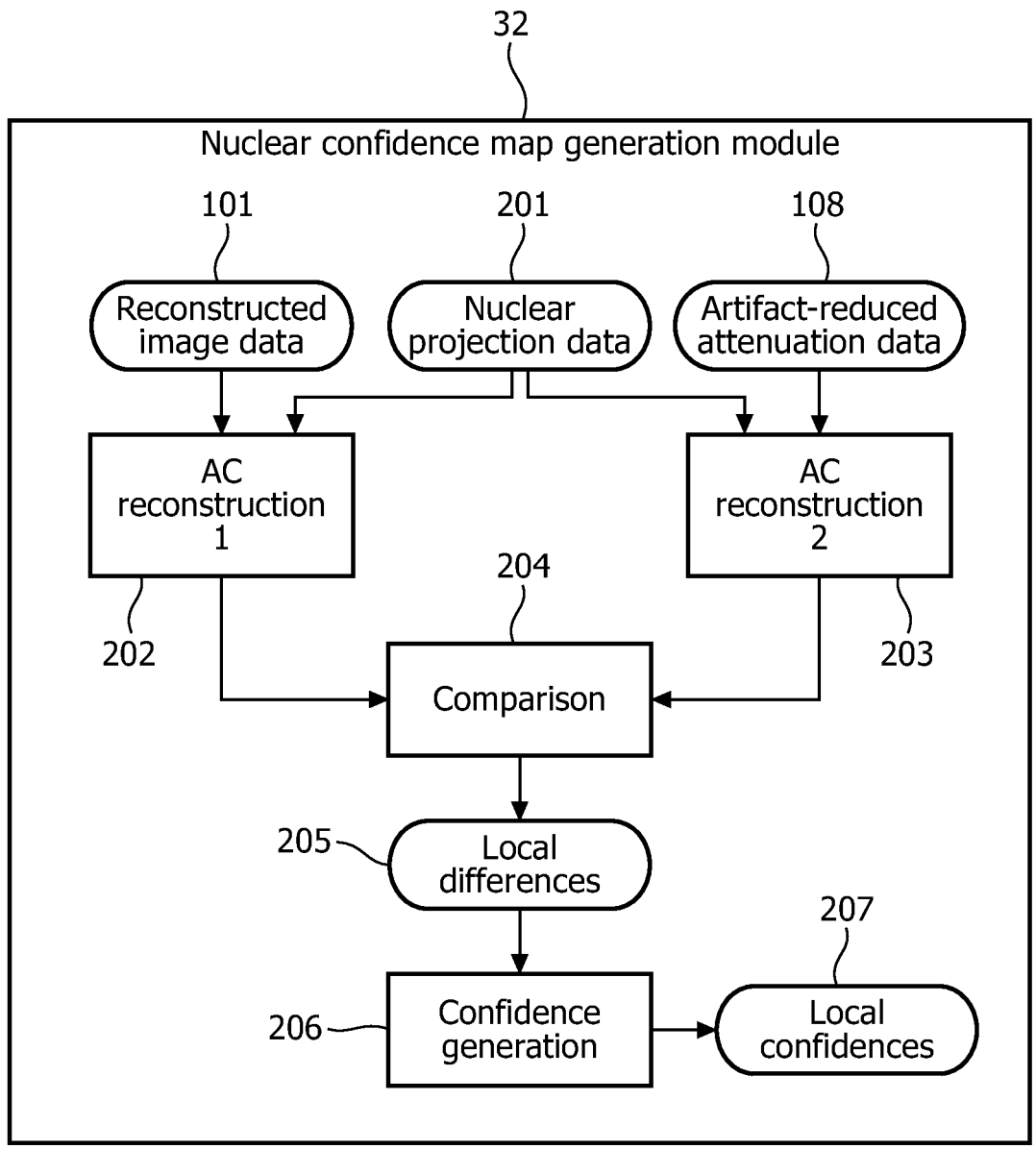
FIG. 3 is an illustration of the nuclear emission image confidence maps module, which is used for the reconstruction of nuclear emission data where structural image data is input for attenuation correction.

FIG. 3 is an illustration of the confidence map generation module for nuclear emission data (e.g., PET or SPECT) 32, when this data is reconstructed with an attenuation correction map obtained from structural imaging as additional input. Nuclear medicine data often includes low-resolution data with values that vary with local tissue status (e.g., density or other tissue properties, metabolic activity, etc.) such that criteria such as anatomical plausibility or the detection of artifact patterns is difficult. Reconstructed structural image data 101 and nuclear projection data 201 are input to a first attenuation-corrected (AC) reconstruction algorithm or module 202 to generate a first attenuation-corrected reconstructed nuclear image. The nuclear projection data 201 and artifact-reduced attenuation data 108 are input to a second AC reconstruction algorithm or module 203 to generate a second attenuation-corrected reconstructed nuclear image. The nuclear emission projection data 201 is thus reconstructed twice 202, 203, using original and artifact-reduced attenuation data as input. A comparison module 204 compares these two independent reconstructions to reveal local differences 205 that are introduced by artifacts in the attenuation maps. The local differences 205 are input to a confidence generation module 206 that determines a local confidence measure or value 207 that indicates uncertainty in the nuclear image reconstruction due to artifacts on the attenuation maps (i.e., reconstructed image 101 and artifact-reduced attenuation data 108) based on the local differences in the two reconstructed nuclear emission images and one or more user-selected parameters. The confidence generation module 206 generates a confidence map 33 (FIG. 1) comprising a confidence value for each voxel that is determined as a function of the local differences in the two reconstructed nuclear emission images and a user-selected parameter. The one or more user-selected parameters determine how a difference in the two reconstructions is interpreted as a local reduction of confidence in the voxel values of the reconstructed image. The confidence map is then overlaid on one or both attenuation corrected nuclear tomographic images and presented to the user.

Figure 4:
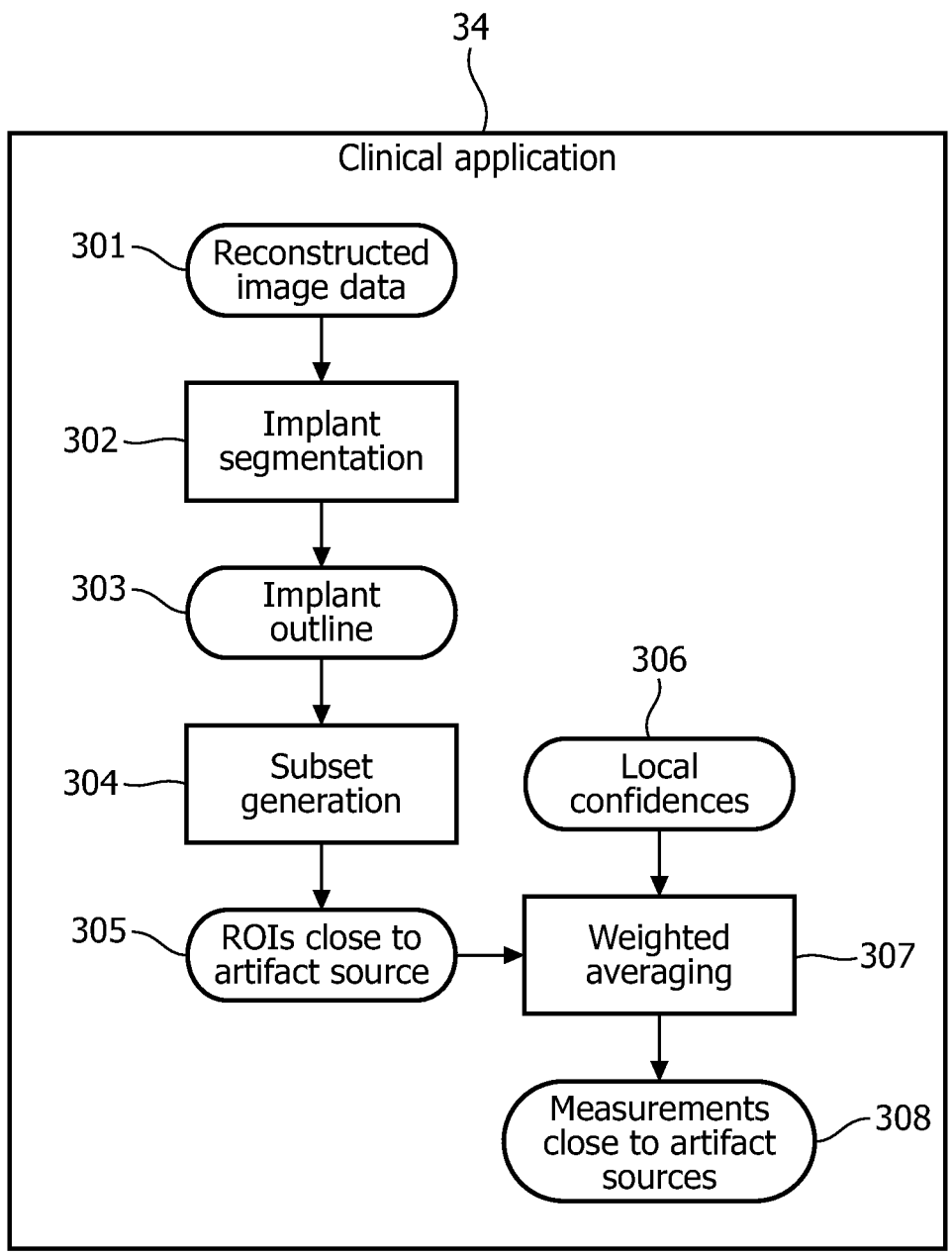
FIG. 4 illustrates an example of a clinical application module or algorithm with which the systems and methods of the preceding figures may be employed.

FIG. 4 illustrates an example of a clinical application module or algorithm 34 with which the systems and methods of the preceding figures may be employed. For instance, the clinical application may apply to assessment of bone density or mass close to a total hip endoprosthesis imaged in CT, as an illustrative example. Although described in this example as pertaining to CT, the module or algorithm 34 represents a protocol that is applicable in similar fashion to SPECT, PET, or CBCT data and to various clinical applications where a quantitative or semi-quantitative assessment of image data close to an artifact source is desired. Such an application may be implemented on a clinical workstation that receives image data from one or more scanners, as described above with regard to FIG. 1. Reconstructed image data 301 and local confidence measures 306 are input for this method. The implant or, more generally, the artifact source is segmented from this image data 302 to provide a 3D outline of the implant in the reconstructed data 303. In one embodiment, a model of the implant is used for a robust and precise detection of the implant. The basic idea for this clinical application is to provide reliable measurements close to an artifact source by binning regions that enable statistically robust averaging. A subset generation module 304 is executed in an application- and implant-specific manner, such that diagnostically relevant information is extracted even when averaging over large regions of interest (ROIs). In the present example, the implant is separated into few regions along the shaft length (upper shaft, lower shaft, etc.), and voxels with similar distances to the implant surface are binned together for each implant region. The exact shape and organization of these binned ROIs 305 depends on the application and implant shape. Diagnostically relevant information is extracted by averaging image values 307 in the binned ROIs, which are weighted by the local confidence map 306.

Figure 5:
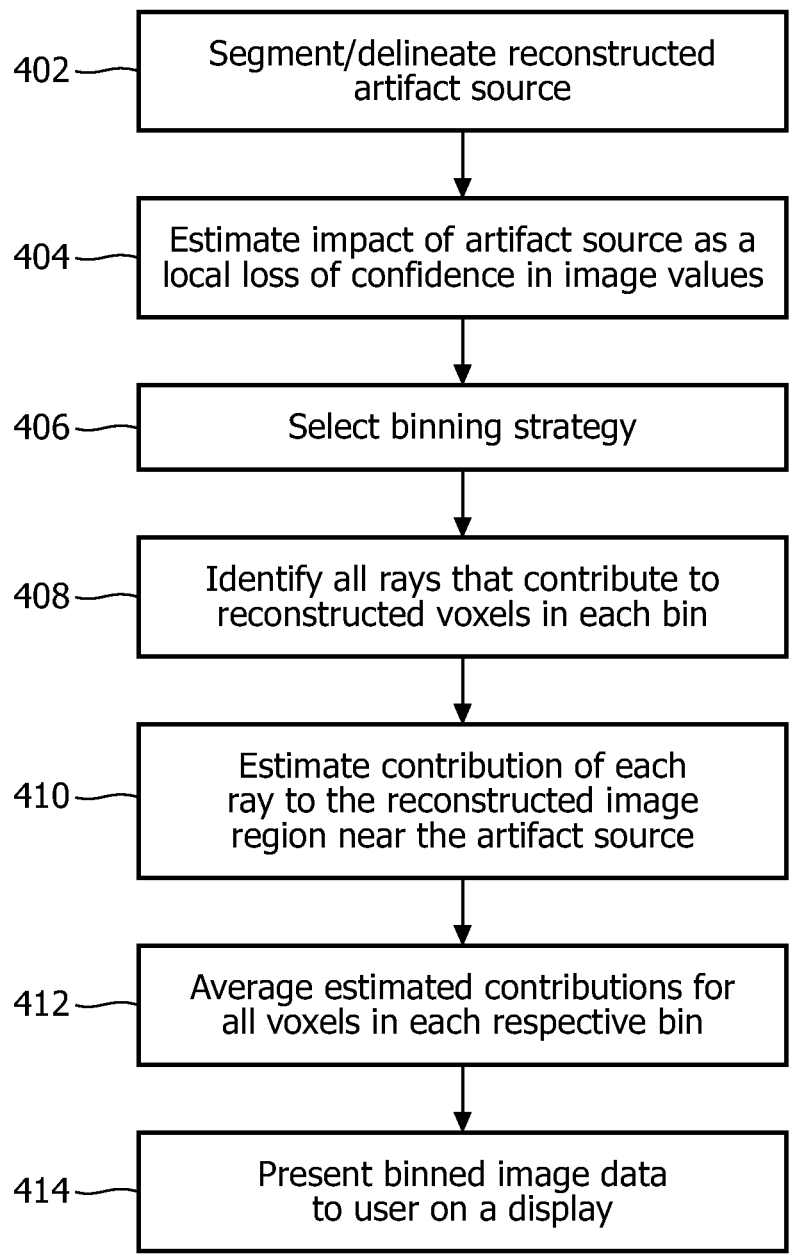
FIG. 5 illustrates a method for improving data reliability or confidence for tomographic image data near an artifact source.

FIG. 5 illustrates a method for improving data reliability or confidence for tomographic image data near an artifact source, such as may be performed by the system of FIG. 1. The method of FIG. 5 is performed after one or more available and known measures for artifact removal have been applied to the tomographic data. However, even after artifact removal, local and global artifacts such blooming and streaks can affect measurements. Therefore, at 402, the artifact source and object of interest is segmented in the reconstruction and (where applicable) the input projection data that allows for its best delineation. For modalities that combine PET or SPECT with CT or CBCT imaging, the radiographic projections are optionally used as additional input. The delineation of the artifact source can use a variety of known methods including intensity or model based segmentation, the alignment to a geometric model of the object of interest, or interactive delineations. The segmentation result in the form of an artifact source outline is then transferred to all input data (e.g., SPECT projections, X-Ray projections, PET lines of response in a sinogram etc.).

After the detection and segmentation of the artifact source, at 404 the impact of the artifact source on image data is estimated as a "local loss of confidence in image values." Methods are known to identify remaining streaks, shading or blooming in an image. The impact of an artifact source further depends on known properties like object thickness, edges, and gradients of object thickness that can be modeled, especially if the shape of the artifact source is known. Therefore, all trusted regions in the image are identified that are not affected by artifacts, and this information can be used to update or modify local confidence maps that were provided by the modules 30 or 32.

At 406, a binning strategy is selected. A first embodiment uses the distance to the object of interest as a binning criterion, so that all voxels that lie in the same distance to the artifact source are binned together. In another embodiment, this binning strategy can be further application- and/or object-dependent. In the example application of a hip endoprosthesis, the binning can be based on the distance to the bone-implant interface surface of the prosthesis shaft (i.e., an artifact sourece) and additionally the axial position along the shaft. Each binning strategy results in a set of data bins where image data of reduced reliability is averaged to obtain final measures of higher reliability. In this manner, the selected binning strategy facilitates automatically binning tomographic values based on specific bins that are defined as a function of an artifact source (e.g., distance to the artifact source or some other suitable criterion).

At this point, an additional, application-specific artifact reduction can be applied. At 408, for each of these bins, all rays (a line integral in CT and CBCT, a line of response in PET etc.) that contribute to the reconstructed voxels in the bin are identified. At 410, for each of these rays, the contribution to the reconstructed image close to the artifact is then estimated. The line integral (activity or attenuation on a ray) is taken from projection data, and then the contributions from all image data outside of this region are subtracted. For the remaining part of a ray that passes through regions affected by an artifact, an average image value is provided, which is affected also by anatomical noise (i.e., local structures along the ray) and has reduced confidence. This averaging of values obtained from projection data can include a confidence value assigned to the projection rays, and the distance that a ray travels through an artifact source is a measure of confidence in a ray, according to one embodiment.

At 412, all estimates in a bin are averaged to obtain a measurement that is less influenced by the image artifact compared to individual reconstructed voxels. Both the averaging of all voxels in a bin and the additional measures obtained from projection rays are preferably weighted by the local confidence measure of artifact impacts and/or the distance that a ray travels through an artifact source. At 414, in addition to the reconstructed data, the object- and artifact-guided binned image data are presented to the user (e.g., on a display, workstation, etc.), preferably together with a visual representation of the regions that were used to bin measurements. For the example application and a first embodiment, these are the two plots "bone density depending on distance to the implant" and "metabolic activity depending on distance to the implant".

In another embodiment, two planar overview images are presented, where color coding can be used to visualize bone density and metabolic activity, preferably next to an image of the implant shaft. For both embodiments, the user selection of a binned measurement (e.g., a mouse click in the plot or overview image) can result in highlighting the regions in the reconstructed image or projections that contributed to this measurement. In addition to this highlighting, the confidence measure can be presented to the user as a map that identifies for each point in the image how much it was affected by image artifacts.

The method of FIG. 5 can be implemented in a clinical workstation application and is useful in combination modalities where a nuclear medicine scanner (SPECT or PET) is combined with a scanner that provides image data for the identification of anatomy and other objects (e.g., CT, CBCT, or MR).

Figure 6:
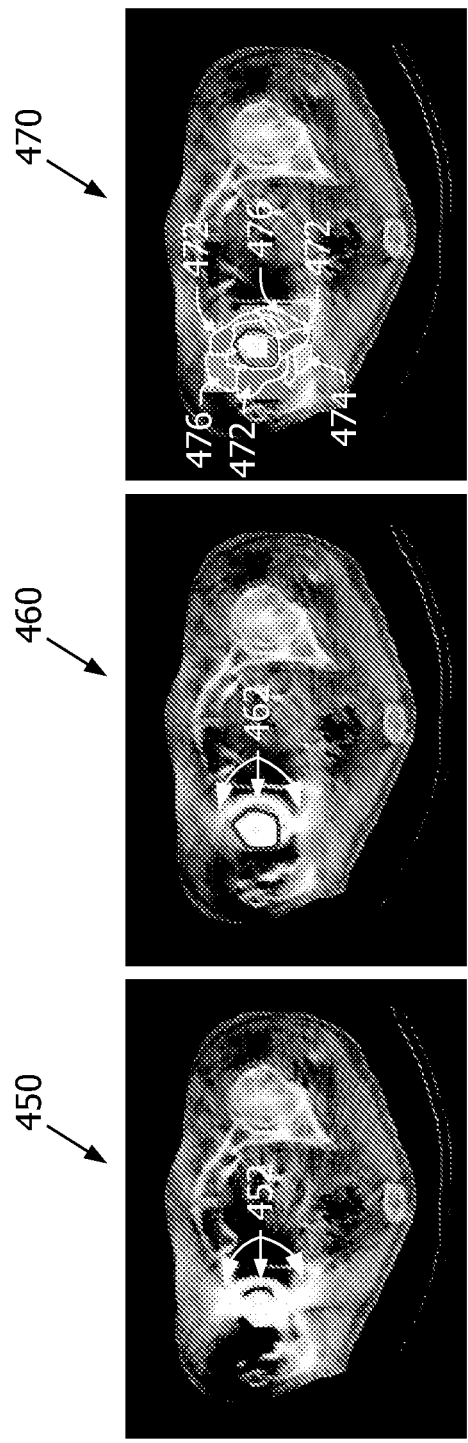
FIGS. 6A-6C show examples of data processed using the described systems and methods.

FIGS. 6A-6C show examples of data processed using the described systems and methods. In FIG. 6A, a CT slice 450 with a total hip endoprosthesis causing strong metal artifacts is shown. Large artifacts 452 are visible in the CT slice 450. Known metal-artifact reduction techniques yield subjective visual improvement as shown by the reduced artifacts 462 in the CT slice 460 of FIG. 6B. In FIG. 6C, a CT slice 470 with color-coded confidence values 472, 474, 476, is shown (e.g., using red, yellow, green, respectively, where red represents minimal confidence, yellow represents moderate confidence, and green represents high confidence, etc., with respect to the data accuracy in the respective region) using overlays that are presented together with the diagnostic image.

Figure 7:
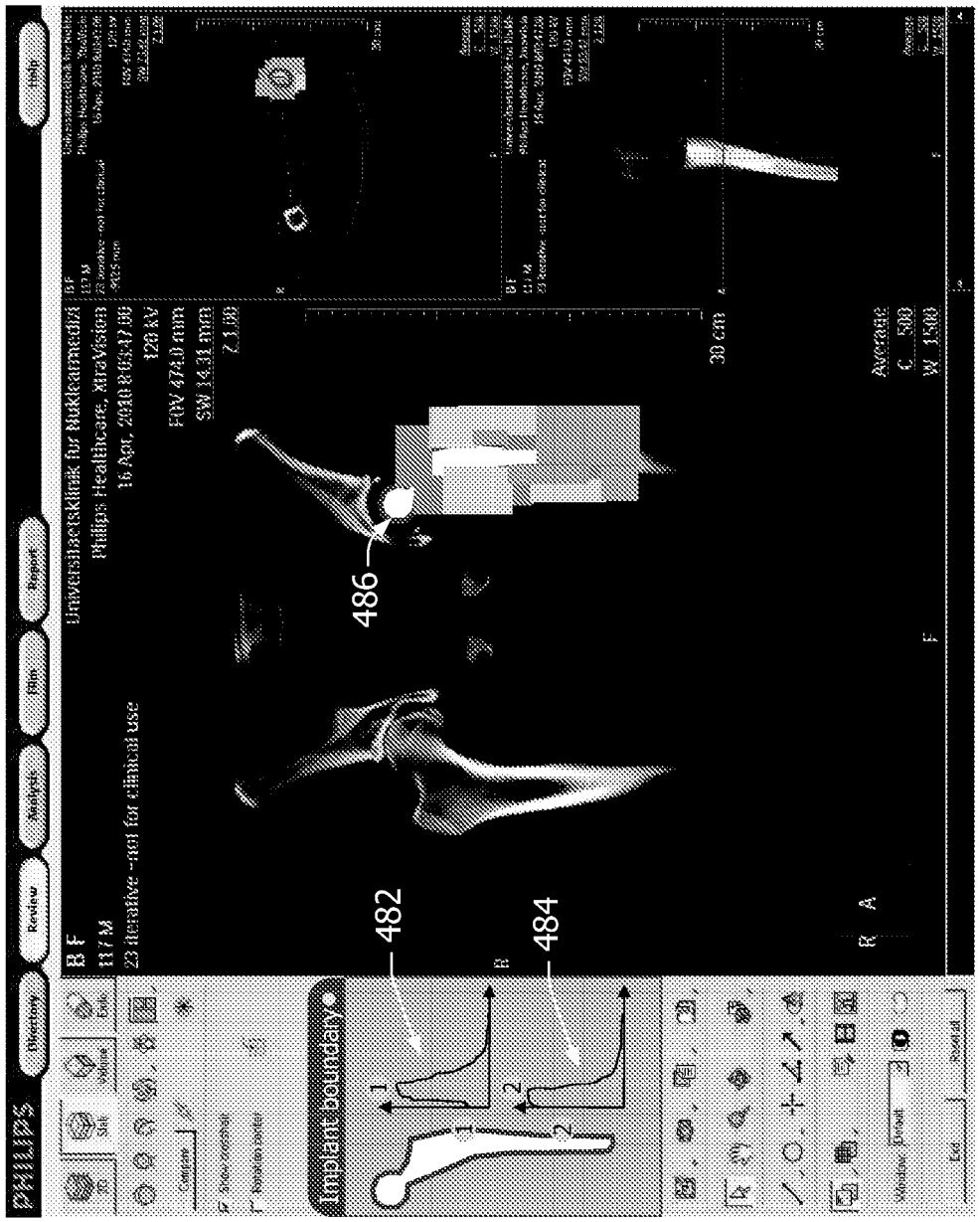
FIG. 7 is a screenshot of a user interface in which plots that are presented to a user show the bone density (in Hounsfield Unit values) for pixels in dependence of their respective distance from the implant, which is indicative of implant fixation in different regions.

FIG. 7 is a screenshot 480 of a user interface in which plots 482, 484, which are presented to a user, show the bone density (Hounsfield Unit values) for pixels in dependence of their respective distance from the implant, which is indicative of implant fixation in different regions (e.g., upper or lower shaft of the implant). Color-coded confidence values 472, 474, 476, are also shown, describing confidence levels for attenuation-corrected pixels as a function of the distance of the respective pixels from the implant or artifact-causing source 486.

In this example embodiment, the segmentation result for the implant and the local confidence are displayed as overlays in a viewing application. Such a user interface can also include user interaction tools to modify or correct the results of automatic segmentation or confidence assignment. The results are presented in an application tab or window that shows the outline of the implant, the regions that have been imaged, and the resulting measurement, in this case the bone density in dependency of the distance to the implant. In the illustrated example, the implant is well anchored in region 2, but a gap between bone and implant is shown in region 1 that would very likely have been obscured by metal artifacts in the original image.

Figure 8:
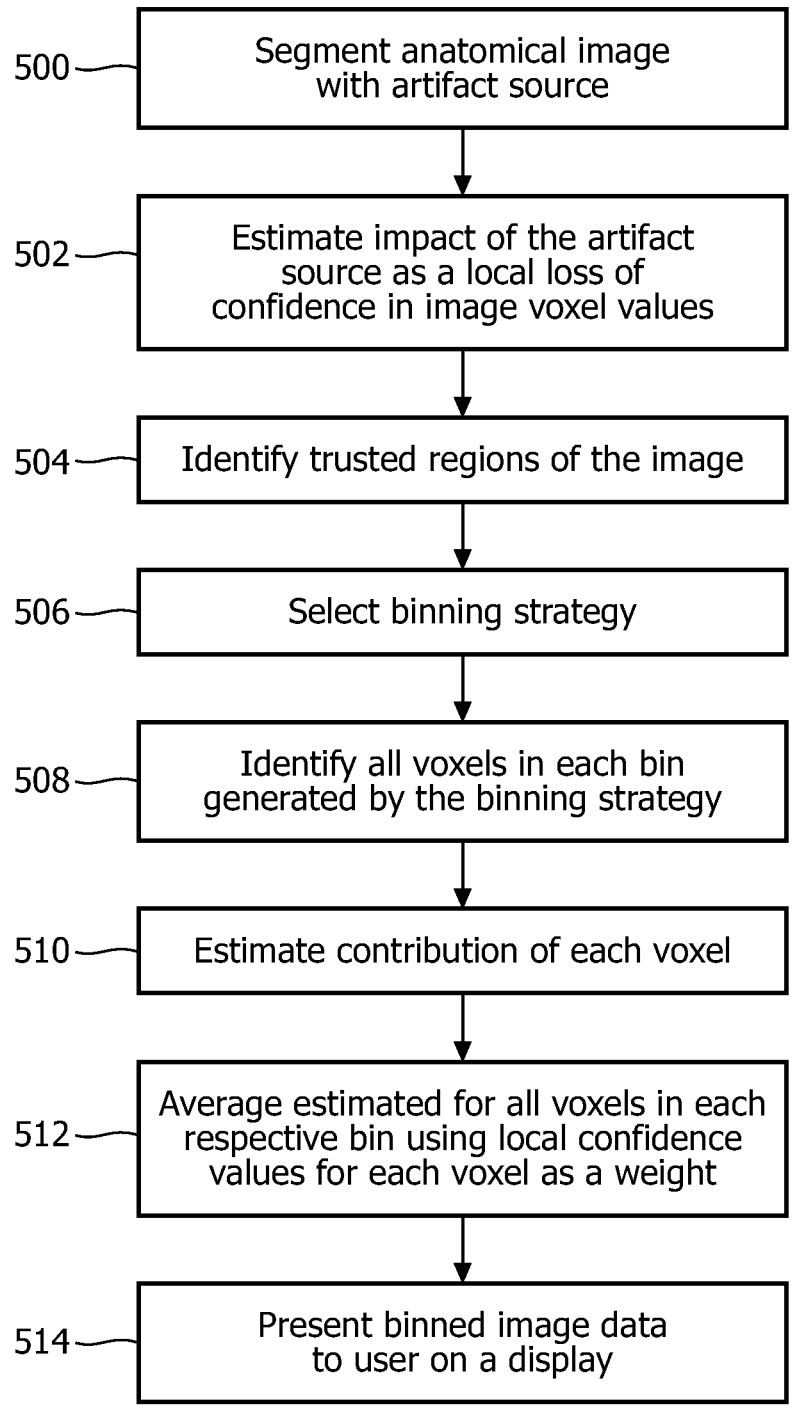
FIG. 8 illustrates a method for improving data reliability for tomographic image data near an artifact source.

FIG. 8 illustrates a method for improving data reliability for tomographic image data near an artifact source. At 500, an anatomical image comprising an artifact source is segmented. At 502, an impact of the artifact source as a local loss of confidence in image voxel values is estimated, for example using the methods described herein and/or based on the segmented artifact source. At 504, trusted regions of the image that are not affected by the artifact source are identified. At 506, a binning strategy is selected for binning similar regions in a reconstructed image together as a function of a clinical application and one or more user-selected parameters. It will be appreciated that acts 500, 502, and 506 are performed in a similar manner to acts 402, 404, and 406 of FIG. 5. At 508, all voxels are identified in each of a plurality of bins generated by the binning strategy. At 510, contribution estimates for all voxels in each bin are estimated. At 512, estimates for all voxels in respective bins are averaged for each bin, using local confidence as a weighting criterion. At 514, binned image data is presented to a user on a display.

It will be appreciated that, in some embodiments, two or more of the different systems, methods, algorithms, etc., described herein can be combined. For instance, local measurements are improved using projection data as described with regard to FIG. 5, and then values for an application-specific region of interest are binned together, such as is described with regard to FIG. 8. It will also be appreciated that the acts described with regard to the methods of FIGS. 5 and 8 are not limited to occurring the order described, but rather may occur in any order that achieves the described outcome(s). Other combinations and/or permutations of features or acts described herein will be apparent to those of skill in the relevant arts.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A method of improving tomographic image quality, comprising:
   automatically binning tomographic values based on application specific bins defined as a function of an artifact source;
   correcting artifacts in a reconstructed image by adjusting voxel values affected by the artifacts in the reconstructed image; and
   generating a confidence map comprising a confidence value for adjusted voxels in each of the bins.

2. The method according to claim 1, wherein the application specific bins are further defined as a function of a clinical application for determining bone density for bone that is next to the artifact source.

3. The method according to claim 1, wherein the application specific bins are defined as a function of a distance to an interface surface between bone tissue and the artifact source.

4. The method according to claim 1, further comprising color-coding the confidence map such that different colors indicate difference levels of confidence in the adjusted voxel values.

5. The method according to claim 1, further comprising comparing measured image voxel values in the reconstructed image to expected image voxel values in order to identify implausible local image voxel values.

6. The method according to claim 1, further comprising detecting the artifacts by performing an artifact pattern recognition procedure.

7. The method according to claim 1, further comprising performing a visible artifact reduction procedure to generate the corrected image.

8. The method according to claim 1, further comprising at least one of:
   displaying the confidence map overlaid on a corrected image; and
   displaying the confidence map next to a corrected image.

9. The method according to claim 1, wherein the voxel values are Hounsfield values.

10. The method according to claim 1, wherein the voxel values are standardized uptake values (SUV) of an emission tomography scan.

11. The method according to claim 1, wherein the reconstructed image is one of a computed tomography (CT) image, a cone-beam or flat panel CT (CBCT) image, a magnetic resonance image (MRI), a positron emission tomography (PET) image, and a single photon emission computed tomography (SPECT) image.

12. The method according to claim 1, further comprising:
   comparing a corrected image to the reconstructed image in order to identify local differences in voxel values;
   combining voxel value contributions from each of implausible local image voxel values, detected artifacts, and local differences in voxel values in order to generate the confidence map for the corrected image; and
   displaying at least one of the confidence map and the corrected image to a user.

13. The method according to claim 12, further comprising weighting local corrections determined from the local differences when generating the confidence map for the corrected image.

14. The method according to claim 12, wherein the confidence value is determined as a function of the voxel value contributions and one or more user-selected parameters.

15. A non-transitory computer-readable medium carrying software for controlling a processor to perform the method according to claim 1.

16. A method of generating a confidence map for a nuclear emission image that is attenuation-corrected using structural image data, comprising:
   generating a first attenuation map from acquired structural image data;
   executing an artifact reduction method on the structural image data to generate artifact-reduced structural image data;
   generating a second attenuation map from the artifact-reduced structural image data;
   executing a first attenuation-corrected reconstruction protocol that reconstructs a set of nuclear emission scan data using the first attenuation map to generate a first attenuation-corrected reconstructed nuclear image;
   executing a second attenuation-corrected reconstruction protocol that reconstructs the set of nuclear scan data using the second attenuation map to generate a second attenuation-corrected reconstructed nuclear image;
   comparing the first and second attenuation-corrected reconstructed nuclear images to identify local differences therein that are introduced by artifacts in the structural image data
   generating a confidence map for the attenuation-corrected nuclear images, the confidence map comprising the local confidence value for each corrected voxel in the second attenuation-corrected nuclear image, the local confidence value being identified as a function of the difference in the first and second reconstructed nuclear emission data and one or more user-selected parameters; and
   displaying at least one of the confidence map and the first or the second attenuation-corrected nuclear image to a user.

17. The method according to claim 16, further comprising color-coding the confidence map such that different colors indicate difference levels of confidence in the corrected voxels.

18. The method according to claim 16, wherein the structural image data is one of regular X-Ray CT data, cone-beam or flat panel CT (CBCT) data, or MRI data, and wherein the nuclear scan data is one of positron emission tomography (PET) data and single photon emission computed tomography (SPECT) data.

19. The method according to claim 16, further comprising at least one of:
   displaying the confidence map overlaid on the first or the second attenuation-corrected nuclear image; and
   displaying the confidence map next to the first or the second attenuation-corrected nuclear image.

20. A non-transitory computer-readable medium carrying software for controlling a processor to perform the method according to claim 16.

21. A system that facilitates generating a confidence map for a nuclear image that is attenuation-corrected using structural scan data, comprising:
   a processor programmed to execute a nuclear confidence map generation module stored in a computer-readable medium and comprising instructions for:
      generating a first attenuation map from acquired structural image data;
      executing an artifact reduction protocol on the structural image data to generate artifact-reduced structural image data;
      generating a second attenuation map from the artifact-corrected structural image data;
      executing a first attenuation-corrected reconstruction protocol that reconstructs a set of nuclear emission scan data using the first attenuation map to generate a first attenuation-corrected reconstructed nuclear image;
      executing a second attenuation-corrected reconstruction protocol that reconstructs the set of nuclear emission scan data using the second attenuation map to generate a second attenuation-corrected reconstructed nuclear image;
      comparing the first and second attenuation-corrected reconstructed nuclear images to identify local differences therein that are introduced by artifacts in the structural image data;
      generating a confidence map for the first or second attenuation-corrected nuclear image, the confidence map comprising the local confidence value for each voxel in the second attenuation-corrected nuclear image, the local confidence value being identified as a function of the local differences in the two reconstructed nuclear emission images and a user-selected parameter; and
      displaying at least one of the confidence map and the first or second attenuation-corrected nuclear image on a display to a user.

22. The system according to claim 21, the instructions further comprising color-coding the confidence map such that different colors indicate difference levels of confidence in the corrected voxels.

23. The system according to claim 21, wherein the structural image data is one of X-Ray computed tomography (CT) data, flat panel or cone-beam CT (CBCT) data and magnetic resonance imaging (MRI) data, and wherein the nuclear scan data is one of positron emission tomography (PET) data and single photon emission computed tomography (SPECT) data.

24. The system according to claim 21, the instructions further comprising at least one of:
   displaying the confidence map overlaid on the first or the second attenuation-corrected nuclear image; and
   displaying the confidence map next to the first or the second attenuation-corrected nuclear image.

25. A method for improving data reliability for tomographic image data near an artifact source, comprising:
   segmenting an anatomical image comprising an artifact source;
   estimating an impact of the artifact source as a local loss of confidence in image voxel values;
   selecting a binning strategy for binning similar regions in a reconstructed image together as a function of a clinical application and one or more user-selected parameters;
   identifying all image elements in each of a plurality of bins generated by the binning strategy;
   averaging the contribution estimates for all voxels in each bin using local confidence values as weighting during averaging; and
   presenting binned image data to a user on a display.

26. A non-transitory computer-readable medium carrying software for controlling a processor to perform the method according to claim 25.

27. A method for providing an improved measurement for a region comprising voxels with low confidence values, comprising:
   segmenting an anatomical image comprising an artifact source;

estimating an impact of the artifact source as a local loss of confidence in image voxel values;
selecting a binning strategy for binning similar regions in a reconstructed image together as a function of a clinical application and one or more user-selected parameters;
collecting, from input projection data, projection rays that pass through a low confidence region:
assigning a confidence value to each projection ray; and
computing a set of new measurements for the low confidence region by removing all contributions to the projection rays from reconstructed image data outside of the low confidence region and assigning the remaining contributions to the low confidence region and computing a final measurement for the low confidence region as weighted average of set of new measurements;
wherein the confidence value is assigned to each projection ray as a weighting function.

28. The method according to claim 27, wherein the user-selected parameter is a distance that each ray travels through the artifact source.

29. The method according to claim 27, wherein the confidence value is a function of the distance that a ray travels through the artifact source.

30. The method according to claim 27, wherein the confidence value is inversely proportional to the distance that a ray travels through the artifact source, such that larger distances correspond to lower confidence values.

31. A non-transitory computer-readable medium carrying software for controlling a processor to perform the method according to claim 27.

* * * * *